United States Patent [19]

Hernandez

[11] 4,017,296

[45] Apr. 12, 1977

[54] PHOSPHONATES FOR CONTROL OF BINDWEED

[75] Inventor: Turney John Hernandez, Centerville, Del.

[73] Assignee: E. I. Du Pont de Nemours and Company, Wilmington, Del.

[22] Filed: Aug. 29, 1975

[21] Appl. No.: 608,908

[52] U.S. Cl. .................................................. 71/86
[51] Int. Cl.² ......................................... A01N 9/36
[58] Field of Search ........................................ 71/86

[56] References Cited

UNITED STATES PATENTS

| | | | |
|---|---|---|---|
| 3,627,507 | 12/1971 | Langsdorf, Jr. | 71/76 |
| 3,819,353 | 6/1974 | Langsdorf, Jr. | 71/76 |
| 3,846,512 | 11/1974 | Langsdorf | 71/76 X |
| 3,849,102 | 11/1974 | Bucha et al. | 71/76 |

*Primary Examiner*—Lewis Gotts
*Assistant Examiner*—Catherine L. Mills

[57] ABSTRACT

This invention relates to a method of controlling bindweed by applying to the locus of the bindweed an effective amount of at least one compound of the formula

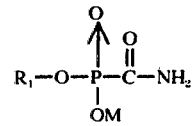

wherein $R_1$ is alkyl of 1 to 3 carbon atoms or allyl; and M is hydrogen, ammonium, sodium, lithium, or potassium.

4 Claims, No Drawings

PHOSPHONATES FOR CONTROL OF BINDWEED

BACKGROUND OF THE INVENTION

U.S. Pat. Nos. 3,627,507, 3,819,353, and 3,846,512 generally teach the use of carbamoylphosphonates as plant growth regulants which are especially useful for controlling the growth of woody vegetation. There is, however, no mention within these patents that certain compounds disclosed therein may control bindweed. Nor is there any mention that they may control bindweed in a unique fashion that is not injurious to desired crop plants such as tomatoes, wheat, soybeans and corn.

The ability to control bindweed is unexpected since this is ordinarily a difficult task and requires the use of powerful herbicides which are injurious to desired crops such as tomatoes.

SUMMARY OF THE INVENTION

In accordance with the instant invention, it has unexpectedly been discovered that certain carbamoylphosphonates control the growth of bindweed. The bindweed is controlled by applying to the locus of the bindweed a compound having the following formula

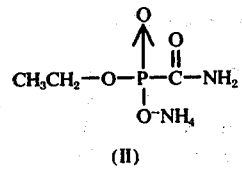

FORMULA I where $R_1$ is alkyl of 1 to 3 carbon atoms or allyl; and M is hydrogen, ammonium, sodium, lithium, or potassium.

Preferred for their higher level of biological activity are those compounds of formula I wherein $R_1$ is methyl or ethyl.

Most preferred for their higher activity and ease of synthesis are those compounds of formula I where M is ammonium.

Particularly preferred for reasons mentioned above are ammonium methyl carbamoyl phosphonate and ammonium ethyl carbamoylphosphonate.

DETAILED DESCRIPTION OF THE INVENTION

Bindweed (Convolvulus spp.) is a noxious weed that infests many acres of crop land. Many compounds are known which can control bindweed, however, these compounds tend not to be feasible for general use because their residues are toxic to crop plants. Unexpectedly, the compounds of the present invention may be applied to the locus of an area infested with bindweed immediately prior to planting desired crops, without substantial injury to crops. That is to say, the compounds of Formula I, which are to be utilized in the method of the instant invention, may be applied just prior to planting crops without any substantial crop injury.

The compounds of formula I are typically applied at rates of from about 4 to 12 kg/ha, more generally, rates from about 2 to 20 kg/ha may be utilized. Generally, application is made in sufficient water to provide good coverage of bindweed leaves and stems.

The process for preparing compounds of formula I is generally taught in the Langsdorf, et al. patent U.S. Pat. No. 3,846,512. A typical procedure for preparing compounds to be utilized in the method of the instant invention is illustrated below for the preparation of ammonium ethyl carbamoylphosphonate, compound II.

$$CH_3CH_2-O-\overset{\overset{O}{\uparrow}}{\underset{O^-NH_4}{P}}-\overset{O}{\overset{\|}{C}}-NH_2$$

(II)

In summary, compound II is prepared by the interaction of the diethyl esters of carboalkoxyphosphonic acids, with ammonium hydroxide; as is illustrated by the following equations:

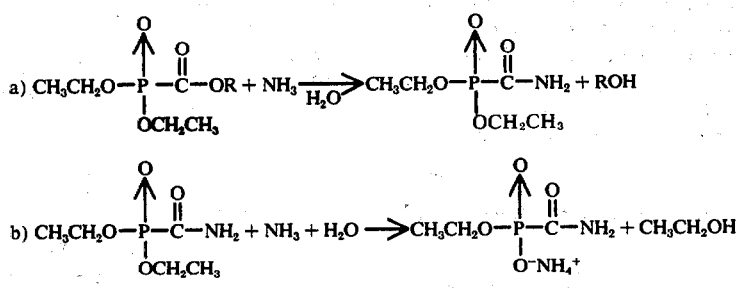

where R is alkyl of one through four carbon atoms, preferably methyl or ethyl.

The following example exemplifies the preparation of ammonium ethyl carbamoylphosphonate; the other compounds of Formula I can be similarly prepared.

EXAMPLE 1

A solution of 48.5 parts of 29% aqueous ammonium hydroxide is stirred and cooled with an external ice bath to 15° C. To the cooled solution 20.5 parts of diethyl carbomethoxyphosphonate is slowly added over a 10 minute period. The mixture turns cloudy, but clears up after about 15 minutes. During this time, the mixture is allowed to warm spontaneously to about 30° C. and stirring is continued for 2 hours. The clear solution is stripped under reduced pressure (15 mm of Hg) at a water-bath temperature of 70° C. The residue is a white crystalline solid which is recrystallized from absolute ethyl alcohol, giving 11.7 parts of ammonium ethyl carbamoylphosphonate, m.m. 173°–176° C.

Agricultural compositions containing compound(s) of formula I, e.g. ammonium ethyl carbamoylphosphonate, can be formulated in the manner similar to that disclosed in U.S. Pat. No. 3,846,512.

Preferred compositions include concentrated solutions in water or in aqueous mixtures of polar solvents such as ethylene glycol or proplyene glycol, low molecular weight alcohols or ketones such as methanol, acetone, methyl ethyl ketone and the like. Other preferred compositions use concentrated water soluble powders of the active ingredient with small amounts of soluble or insoluble anticaking agents. Such compositions can be mixed in the concentrated form, or upon dilution for spray application, with additives such as thickeners, binders, spreaders, stickers, corrosion inhibitors, antifoam agents, etc. or with spray-marking agents (such as pigments) to clearly mark loci that have been or are being treated.

Generally, compositions to be used in the process of this invention, may contain as a conditioning agent one or more surface-active agents, sometimes called surfactants, in amounts sufficient to render a given composition containing the compound of this invention more readily soluble in water or capable of wetting foliage efficiently.

The surface-active agent used in this invention can be a wetting, dispersing or an emulsifying agent which will assist dispersion and solution of the active compound. The surface-active agent or surfactant can include such anionic, cationic and non-ionic agents as have heretofore been generally employed in plant control compositions of similar type. Suitable surface-active agents are set forth, for example in "Detergents and Emulsifiers" 1972 Annual by John W. McCutcheon, Inc.

In general, less than 10% by weight of the surface-active agent will be used in compositions of this invention and ordinarily the amount of surface-active agents will range from about 1–5% but may even be less than 1 % by weight, e.g. 0.1 to 0.9 weight percent.

The following example teaches a useful formulation of the subject compound:

EXAMPLE 2

A solution of the following formula is prepared:

| | |
|---|---|
| Ethyl ammonium carbamoylphosphonate | 42% |
| Water | 58% |

The above components are blended to form a stable, homogeneous solution containing 4 lb/gal. of active ingredient.

The following example illustrates the efficacy of the compounds of formula I for bindweed control.

EXAMPLE 3

4.5 Kilograms of ammonium ethyl carbamoylphosphonate were mixed with 1892 liters of an aqueous solution containing 0.25% of surfactant WK (dodecyl ether of polyethylene glycol) and applied to a 0.47 hectare area infested with bindweed. Two weeks later the bindweed in the treated area was not flowering whereas bindweed in adjacent untreated plots was flowering profusely. Seven weeks later, the bindweed foliage on treated plants appeared to be necrotic. The treated plot remained free of bindweed throughout the following year.

I claim:

1. A method for the retardation of bindweed on cropland which comprises applying to the foliage of the bindweed an effective amount of a compound selected from the compounds having the formula

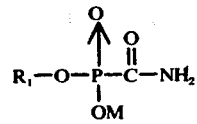

wherein
$R_1$ is alkyl of 1 to 3 carbon atoms or allyl; and
M is hydrogen, ammonium, sodium, lithium, or potassium,
and then proceeding immediately to plant crops on said cropland whereby there is substantially no injury to said crops.

2. The process of claim 1 wherein $R_1$ is methyl or ethyl.

3. The process of claim 1 wherein the compound is ammonium methyl carbamoylphosphonate.

4. The process of claim 1 wherein the compound is ammonium ethyl carbamoylphosphonate.

* * * * *